United States Patent [19]

Connell et al.

[11] Patent Number: 5,116,934
[45] Date of Patent: May 26, 1992

[54] POLYIMIDAZOLES VIA AROMATIC NUCLEOPHILIC DISPLACEMENT

[75] Inventors: John W. Connell; Paul M. Hergenrother, both of Yorktown, Va.

[73] Assignee: The United States of America as represented by the Administrator of the National Aeronautics and Space Administration, Washington, D.C.

[21] Appl. No.: 732,884

[22] Filed: Jul. 19, 1991

Related U.S. Application Data

[62] Division of Ser. No. 508,316, Apr. 12, 1990, Pat. No. 5,066,811.

[51] Int. Cl.$^5$ .................................................. C08G 8/02
[52] U.S. Cl. .................................... 528/125; 528/126; 528/127; 528/128; 528/220; 528/224; 528/228; 528/401
[58] Field of Search ............... 528/125, 126, 127, 128, 528/220, 224, 228, 401

[56] References Cited

U.S. PATENT DOCUMENTS 5,066,811 11/1991 Connell et al. .................... 548/119

OTHER PUBLICATIONS

Radlmann et al., Chem. Abs. vol. 75, No. 26, 152165u.
Kuenzel et al., Chem. Abs. vol. 72, No. 4, 68047n.
Fargerfabriken, Chem. Abs. vol. 72, No. 12, 56103q.

*Primary Examiner*—John Kight, III
*Assistant Examiner*—Sam A. Acquah
*Attorney, Agent, or Firm*—George F. Helfrich

[57] ABSTRACT

Polyimidazoles (PI) are prepared by the aromatic nucleophilic displacement reaction of di(hydroxyphenyl)imidazole monomers with activated aromatic dihalides or activated aromatic dinitro compounds. The reactions are carried out in polar aprotic solvents such as N,N-dimethylacetamide, sulfolane, N-methylpyrrolidinone, dimethylsulfoxide, or diphenylsulfone using alkali metal bases such as potassium carbonate at elevated temperatures under nitrogen. The di(hydroxyphenyl)imidazole monomers are prepared by reacting an aromatic aldehyde with a dimethoxybenzil or by reacting an aromatic dialdehyde with a methoxybenzil in the presence of ammonium acetate. The di(methoxyphenyl)imidazole is subsequently treated with aqueous hydrobromic acid to give the di(hydroxyphenyl)imidazole monomer. This synthetic route has provided high molecular weight PI of new chemical structure, is economically and sythetically more favorable than other routes, and allows for facile chemical structure variation due to the availability of a large variety of activated aromatic dihalides and dinitro compounds.

7 Claims, No Drawings

POLYIMIDAZOLES VIA AROMATIC NUCLEOPHILIC DISPLACEMENT

ORIGIN OF THE INVENTION

This is a divisional of copending application Ser. No. 07/508,316 filed Apr. 12, 1990, now U.S. Pat. No. 5,066,811.

The invention described herein was made by employees of the United States Government and may be manufactured and used by or for the Government for governmental purposes without the payment of any royalties thereon or therefor.

BACKGROUND OF THE INVENTION

1. Field of the Invention

This invention relates to structural resins and in particular to new polyimidazoles formed from the aromatic nucleophilic displacement reaction of novel di(hydroxyphenyl)imidazole monomers with activated aromatic dihalides or activated aromatic dinitro compounds, whereby economically produced, high molecular weight polyimidazoles useful as adhesives, coatings, films, membranes, moldings, and composite matrices are obtained.

2. Description of the Related Art

Polyimidazoles (PI) are heterocyclic polymers which were synthesized by the reaction of bis(phenyl-α-diketone) with an aromatic dialdehyde in the presence of ammonia as represented below:

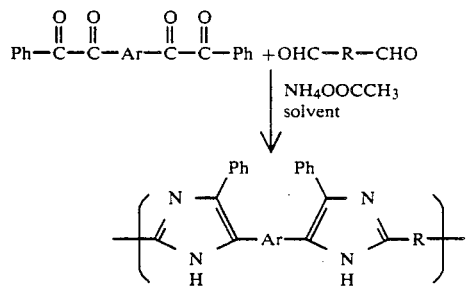

where Ar is a divalent aromatic radical such as

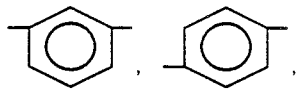

etc. R is a divalent aromatic radical which may be

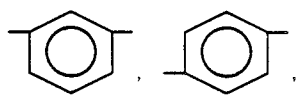

etc.

The synthesis and characterization of PI was first described in 1967 [V. B. Krieg and G. Manecke, *Die Makromolekulare Chemie*, 108,210 (1967)]. The polymers were of relatively low molecular weight, and only a few physical properties were determined. PI prepared by the reaction of bis(phenyl-α-diketone) with aromatic dialdehydes in the presence of ammonia generally are of low molecular weight, presumably due to side reactions. Therefore, there are relatively few reports concerning the preparation and characterization of these materials.

SUMMARY OF THE INVENTION

The present invention constitutes new compositions of matter and a new process to prepare polyimidazoles (PI). It concerns new PI, novel monomers, and the process for preparing the same.

Another object of the present invention is to provide new PI that are useful as adhesives, coatings, films, membranes, moldings, and composite matrices.

Another object of the present invention is to provide several new di(hydroxyphenyl)imidazole monomers.

According to the present invention the foregoing and additional objects are obtained by synthesizing PI by the nucleophilic displacement reaction of di(hydroxyphenyl)imidazole monomers with activated aromatic dihalides. The inherent viscosities ($\eta_{inh}$) of the PI ranged from 0.24 to 1.38 dL/g, and the glass transition temperatures (Tg) ranged from 230° C. to 318° C. Thermogravimetric analysis showed no weight loss occurring below 300° C. in air or nitrogen with a five percent weight loss occurring at about 400° C. in air and at about 495° C. in nitrogen.

The synthesis of PI involved the use of di(hydroxyphenyl)imidazole monomers of two different types; those prepared from monoaldehydes as shown in Equation (1), and those prepared from dialdehydes as depicted in Equation (2).

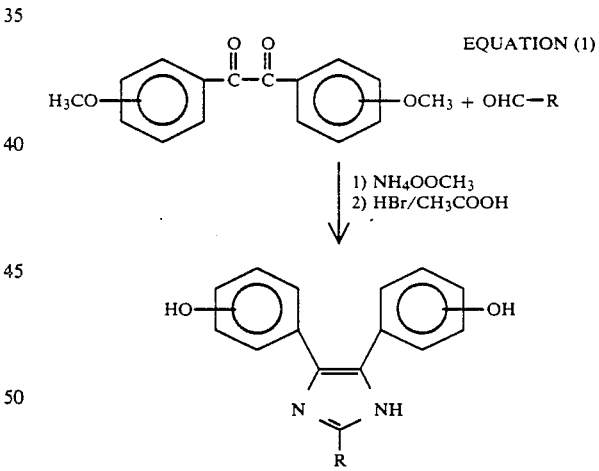

EQUATION (1)

where R can be H, $CH_2CH_3$, $OCH_3$, $CH_3$, $CF_3$,

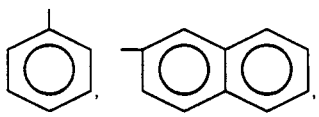

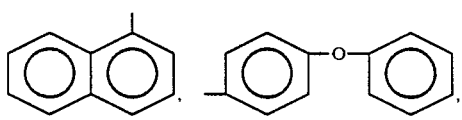

-continued

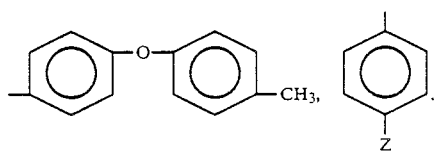

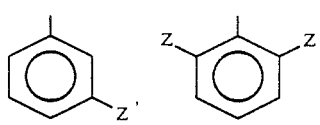

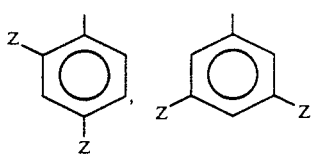

where Z can be $CH_3$, $CF_3$, $OCH_3$, Ph, $NO_2$, I, Cl, Br, F, and $CH_2CH_3$. The catenation of the hydroxy group may be meta meta, para para, or meta para.

The general reaction sequence for the preparation of the di(hydroxyphenyl)imidazoles prepared from dialdehydes is represented in Equation (2).

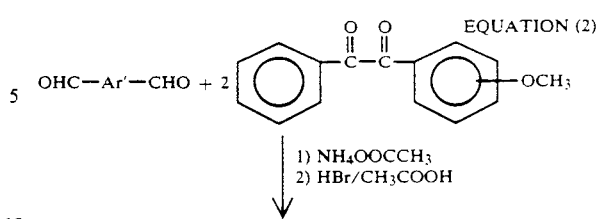

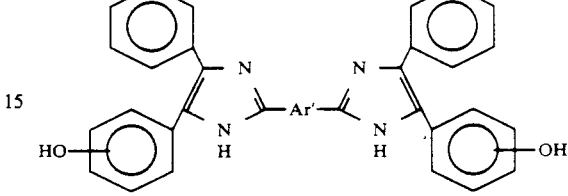

Where Ar' is

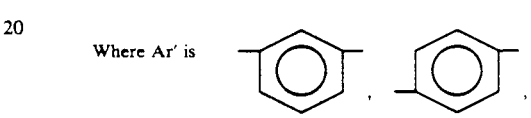

Where G is nil, $CH_2$, O, S, C=O, $SO_2$.

The catenation of the hydroxy group may be meta meta, para para or meta para.

The general reaction sequence for the synthesis of PI is represented below:

EQUATION (3)
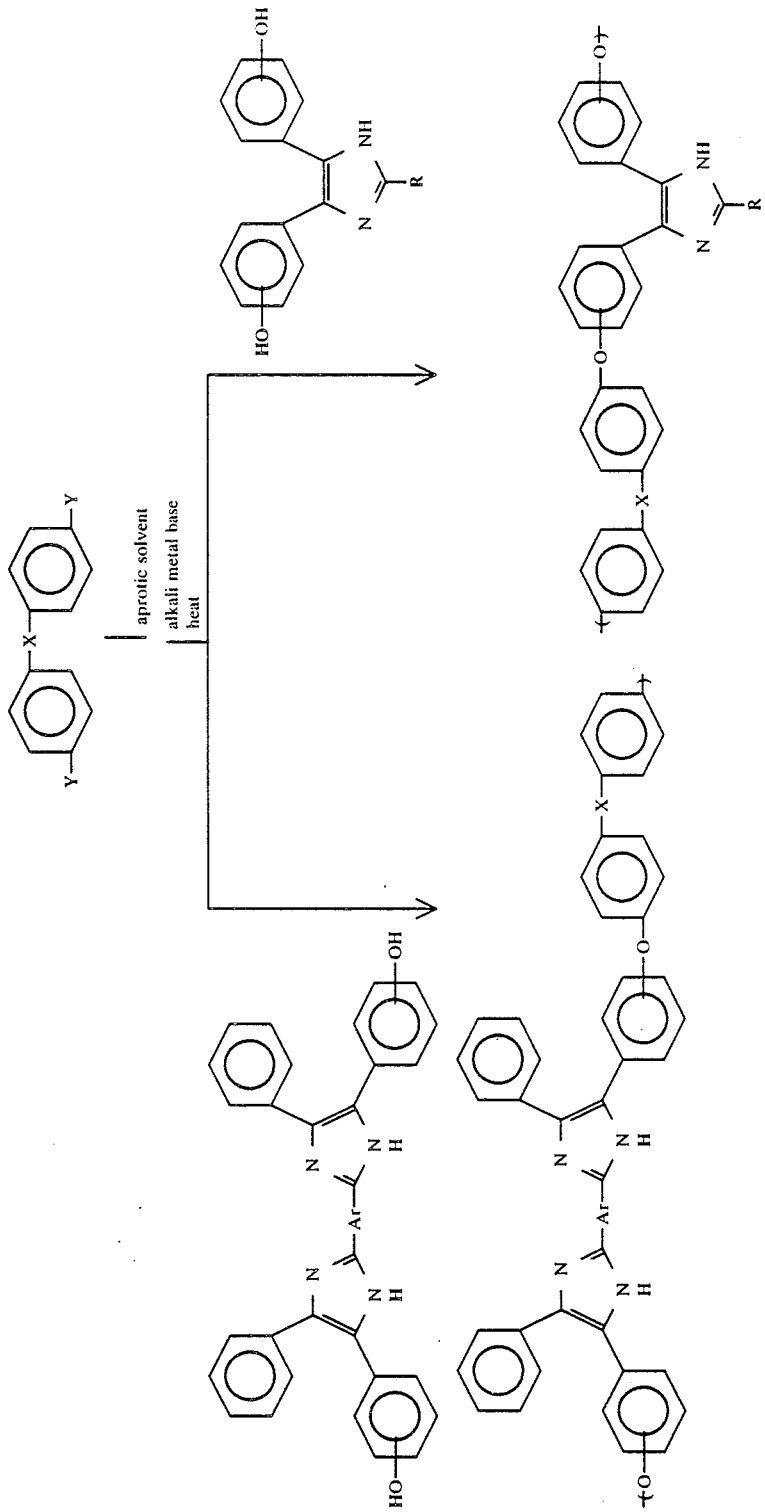
Where Y can be Cl, F, or NO₂ where R can be H, CH$_3$, CH$_2$CH$_3$, OCH$_3$, CF$_3$

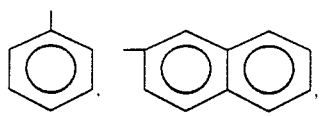

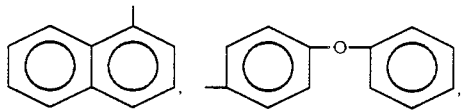

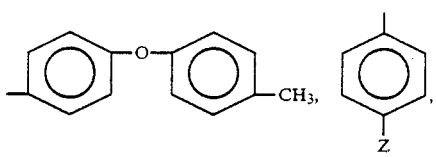

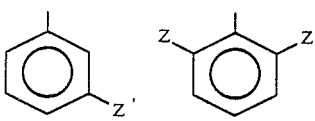

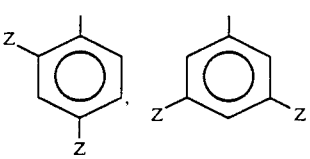

where Z can be CH$_3$, CF$_3$, OCH$_3$, Ph, NO$_2$, I, Cl, Br, F, CH$_2$CH$_3$, etc. Where Ar can be

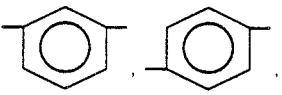

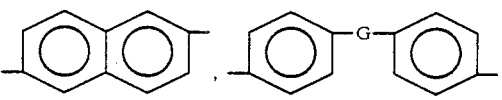

Where G can be nil, CH$_2$, O, S, C=O, SO$_2$.

The substitution of the hydroxy group may be meta meta, para para, or meta para, and X can be

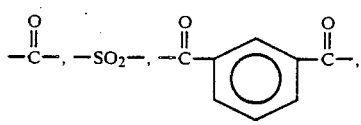

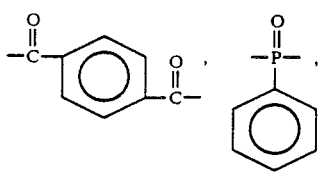

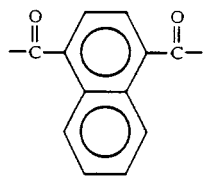

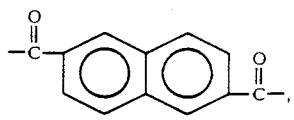

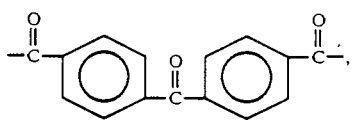

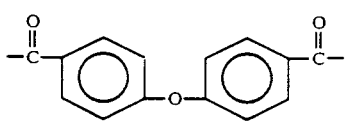

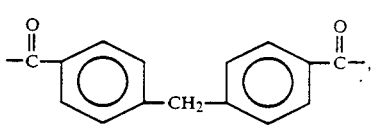

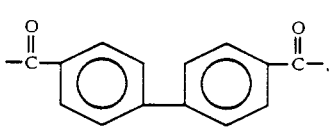

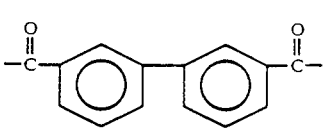

DESCRIPTION OF THE PREFERRED EMBODIMENTS

Having generally described the invention, a more complete understanding thereof can be obtained by reference to the following specific examples which are provided herein for purposes of illustration only and do not limit the invention.

EXAMPLES

EXAMPLE 1

The following example illustrates the reaction sequence for the synthesis of a polyimidazole where R is a phenyl group and X is terephthaloyl and Y is F (see Equation (3)).

MONOMER SYNTHESIS 4,5-Bis(4-hydroxyphenyl)-2-phenylimidazole

Into a one liter three neck round bottom flask equipped with a mechanical stirrer, thermometer, nitrogen inlet and reflux condenser was placed 4,4'-dimethoxybenzil (13.53 g, 0.05 mol) and acetic acid (300 ml). The mixture was stirred with heating to give a yellow solution. Ammonium acetate (68.0 g, 0.88 mol) and benzaldehyde (26.0 g, 0.25 mol) were added along with additional acetic acid (100 ml). The solution was heated to reflux (about 120° C.) overnight under nitrogen. The orange solution was cooled and poured into water to give an off-white precipitate which was collected, washed repeatedly with water and dried at 125° C. Yield was 17.5 g (98%) of white solid. Recrystallization from ethanol/water (3:1) gave 15.8 g (89%) of white crystals, m.p. 198°-200° C.

4,5-Bis(4-methoxyphenyl)-2-phenylimidazole (15.8 g, 0.044 mol) was placed in a 250 ml three neck round bottom flask equipped with a mechanical stirrer, nitrogen inlet, thermometer, reflux condenser and hydrogen bromide gas trap along with acetic acid (75 ml) and 47-49% aqueous hydrogen bromide solution (130 ml). The mixture was heated to reflux for 16 hours, cooled, poured into water to give a white solid, which was neutralized with sodium hydroxide, collected, washed with water and dried at 100° C. Yield was 13.7 g of white solid. Recrystallization from ethanol/water (3:1) gave 11.5 g (79%) of white crystals, m.p. 327°-330° C. Anal. Calcd. for $C_{21}H_{16}N_2O_2$: C, 76.80%; H, 4.91%; N, 8.53%. Found: C, 76.50%; H, 5.00%; N, 8.44%.

POLYIMIDAZOLE SYNTHESIS

Into a 100 ml three neck round bottom flask equipped with a mechanical stirrer, thermometer, nitrogen inlet, moisture trap and reflux condenser was placed 4,5-bis(4-hydroxyphenyl)-2-phenylimidazole (2.4267 g, 7.5 mmol), 1,4-bis(4-fluorobenzoyl)benzene (2.4173 g, 7.5 mmol), pulverized anhydrous potassium carbonate (2.4 g, 17.0 mmol, 15% excess), dry N,N-dimethylacetamide (DMAc) (20 ml, 20% solids) and toluene (30 ml). The mixture was heated to about 135° C. for four hours and then heated to 155° C. overnight under nitrogen. The viscous dark red solution was diluted with DMAc (20 ml) and precipitated into water/acetic acid mixture, collected, washed successively in water and methanol and dried at 125° C. Yield was 4.4 g (97%) of yellow polymer with a glass transition temperature of 248° C. The inherent viscosity of a 0.5% solution in DMAc at 25° C. was 0.89 dL/g. Thin films cast from DMAc solution gave tensile strength, tensile modulus and elongation at 25° C. of 14,200 psi, 407,000 psi and 6.0%; at 177° C. of 8,200 psi, 306,000 psi and 6.0%; and at 200° C. of 6,600 psi, 273,500 psi and 7.5%.

EXAMPLE 2

The following example illustrates the reaction sequence for the synthesis of the polyimidazole where R is a phenyl group, X is a carbonyl group, and Y is F (see Equation (3)).

Into a 100 ml three neck round bottom flask equipped with a mechanical stirrer, thermometer, nitrogen inlet, moisture trap and reflux condenser was placed 4,5-bis(4-hydroxyphenyl)-2-phenylimidazole (3.2836 g, 10.0 mmol), 4,4'-difluorobenzophenone (2.1819 g, 10.0 mmol), pulverized anhydrous potassium carbonate (3.2 g, 23.0 mmol, 15% excess), dry DMAc (22 ml, 20% solids) and toluene (35 ml). The mixture was heated to about 135° C. for four hours and then heated to 155° C. overnight under nitrogen. The viscous dark red solution was diluted with DMAc (20 ml) and precipitated into water/acetic acid mixture, collected, washed successively in water and methanol and dried at 125° C. Yield was 5.0 g (99%) of off-white polymer with a glass transition temperature of 259° C. The inherent viscosity of a 0.5% solution in DMAc at 25° C. was 0.61 dL/g. Thin films cast from DMAc solution gave tensile strength, tensile modulus and elongation at 25° C. of 13,300 psi, 405,200 psi and 5.0% and at 177° C. of 9,500 psi, 400,500 psi and 3.4% respectively.

EXAMPLE 3

The following example illustrates the reaction sequence for the synthesis of the polyimidazole where Ar' is 1,4-phenylene, X is isophthaloyl and Y is F (See Euation 3).

MONOMER SYNTHESIS 1,4-Bis[2-imidazolyl-4-(4-hydroxyphenyl)-5-(phenyl)]-benzene

Into a 500 ml three neck round bottom flask equipped with a mechanical stirrer, thermometer, nitrogen inlet and reflux condenser was placed 4-hydroxybenzil (9.05 g, 0.04 mol) and acetic acid (100 ml). The mixture was stirred with heating to give a yellow solution. Terephthalaldehyde (2.68 g, 0.02 mol) was subsequently added along with ammonium acetate (43.1 g, 0.56 mol) and acetic acid (50 ml). The mixture was stirred with heating and within one hour a yellow precipitate formed. The mixture was then heated to reflux (about 120° C.) for six hours. The mixture was cooled and poured into ice water, and the yellow solid collected, washed with water, and dried at 100° C. Yield was 10.7 g (98%). The solid was recrystallized from N,N-dimethylformamide (100 ml) and water (25 ml) using activated charcoal to give 8.6 g (79%) of yellow solid, m.p. about 390° C. Anal. Calcd for $C_{36}H_{26}N_4O_2$: C, 79.10%; H, 4.79%; N, 10.25%. Found: C, 78.81%; H, 4.87%; N, 10.12%.

POLYIMIDAZOLE SYNTHESIS

Into a 100 ml three neck round bottom flask equipped with a mechanical stirrer, thermometer, nitrogen inlet, moisture trap and reflux condenser was placed 1,4-bis[2-imidazolyl-4-(4-hydroxyphenyl)-5-(phenyl)]benzene (2.7330 g, 0.005 mol), 1,3-bis(4-fluorobenzoyl)benzene (1.6115 g, 0.005 mol), pulverized anhydrous potassium carbonate (1.6 g, 0.0115 mol, 15% excess), dry DMAc (18 ml, 18% solids) and toluene (25 ml). The mixture was heated to about 135° C. for four hours, and then heated to 155° C. overnight under nitrogen. The viscous dark red solution was diluted with DMAc (20 ml) and precipitated into water/acetic acid mixture, collected, washed successively in water and methanol and dried at 125° C. Yield was 4.04 g (97%) of yellow polymer with a glass transition temperature of 273° C. The inherent viscosity of a 0.5% solution in DMAc at 25° C. was 1.38 dL/g. Thin films cast from m-cresol solution gave tensile strength, tensile modulus and elongation at 25° C. of 17,600 psi, 464,000 psi and 8.1%, at 93° C. of 15,300 psi, 402,000 psi and 5.6% and at 232° C. of 7400 psi, 285,300 psi and 4.8% respectively.

Polymer characterization is presented in Table 1, and thin film and adhesive properties are presented in Table 2 and Table 3, respectively.

TABLE 1
POLYMER CHARACTERIZATION

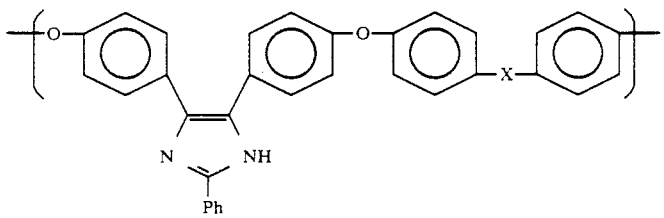

| POLYMER | X | INHERENT[1] VISCOSITY, dL/g | GLASS TRANSITION[2] TEMPERATURE, °C. |
|---|---|---|---|
| P1 | −P(=O)(Ph)− | 0.24 | 318 |
| P2 | SO₂ | 0.41 | 277 |
| P3 | CO | 0.61 | 259 |
| P4 | −C(=O)−C₆H₄−C₆H₄−C(=O)− (biphenyl dicarbonyl) | 0.53 | 258 |
| P5 | −C(=O)−naphthyl−C(=O)− | 0.40 | 248 |
| P6 | −C(=O)−C₆H₄−C(=O)− (para) | 0.89 | 248 |
| P7 | −C(=O)−C₆H₄−C(=O)−C₆H₄−C(=O)− | 0.49 | 239 |
| P8 | −C(=O)−C₆H₄−CH₂−C₆H₄−C(=O)− | 0.58 | 231 |
| P9 | −C(=O)−C₆H₄−O−C₆H₄−C(=O)− | 0.64 | 230 |
| P10 | −C(=O)−C₆H₄−C(=O)− (meta) | 0.55 | 230 |

TABLE 2

THIN FILM PROPERTIES[1]

| POLYMER | TEST TEMP., °C. | TENSILE STRENGTH, KSI | TENSILE MODULUS, KSI | ELONG., % |
|---|---|---|---|---|
| P3 | 25 | 13.3 | 405.2 | 5.0 |
|    | 177 | 9.5 | 400.0 | 3.4 |
| P6 | 25 | 14.2 | 407.0 | 6.0 |
|    | 177 | 8.2 | 306.0 | 6.0 |
|    | 200 | 6.6 | 273.0 | 7.5 |
| P7 | 25 | 13.8 | 390.0 | 6.3 |
|    | 177 | 8.4 | 285.0 | 6.2 |
| P10 | 25 | 12.0 | 362.4 | 4.0 |
|     | 177 | 8.3 | 336.4 | 3.8 |

[1]Tested according to ASTM D882, average of four specimens per test condition.

TABLE 3

ADHESIVE PROPERTIES*

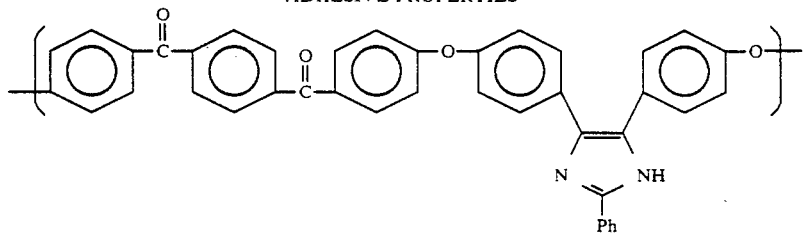

| BONDING CONDITIONS | TEST TEMP., °C. | TI/TI TENSILE SHEAR STRENGTH, PSI | FAILURE MODE |
|---|---|---|---|
| 300° C., 100 PSI, 1 HR | 25 | 4660 | 50% COHESIVE |
| 300° C., 500 PSI, 1 HR | 25 | 4120 | 20% COHESIVE |
| 300° C., 200 PSI, 1 HR | 25 | 4810 | 75% COHESIVE |
| " | 93 | 3800 | 30% COHESIVE |
| " | 177 | 3700 | 40% COHESIVE |
| " | 200 | 3050 | 45% COHESIVE |

*Tested according to ASTM D1002, average of four specimens per test.
Inherent viscosity of polymer 0.57 dL/g, glass transition temperature 245° C.

What is new and desired to be secured by Letters Patent of the United States is:

1. A process for synthesizing polyimidazoles by aromatic nucleophilic displacement, which comprising reacting a di(hydroxyphenyl)imidazole with an activated aromatic dihalide or dinitro compound having the general structure:

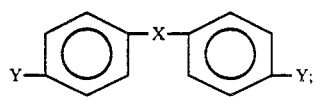

wherein X is a radical selected from the group consisting of:

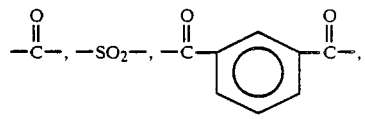

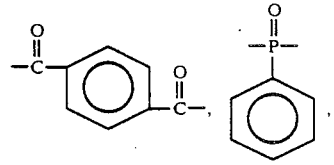

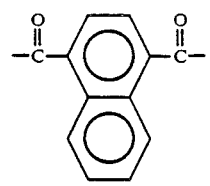

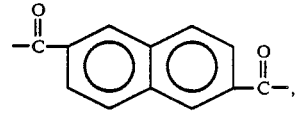

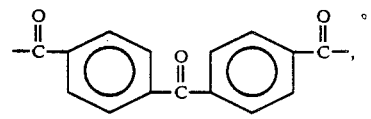

-continued

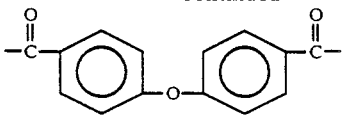

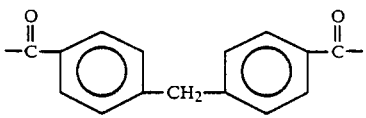

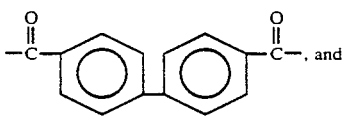, and

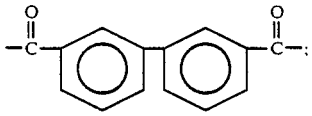

wherein Y is selected from the group consisting of:

Cl, F, and NO$_2$;

wherein said reaction is carried out in a polar aprotic solvent selected from the group consisting of:
N,N-dimethylacetamide,
N,-methylpyrrolidinone,
sulfolane,
diphenylsulfone,
N-cyclohexylpyrrolidinone, and
dimethylsulfoxide;
wherein said reaction is carried out in the presence of an alkali metal base; and wherein said reaction is carried out with the application of heat.

2. The method of claim 1, wherein R is a phenyl group.

3. The method of claim 1, wherein Ar' is 1,4-phenylene.

4. The method of claim 1, wherein Ar' is 1,4-phenylene and X is isophthaloyl.

5. The method of claim 1, wherein Y is selected from the group consisting of F and Cl.

6. The method of claim 5, wherein Y is F.

7. The method of claim 1, wherein the solvent is N,N-dimethylacetamide.

* * * * *